US008877456B2

(12) United States Patent
Pickett et al.

(10) Patent No.: US 8,877,456 B2
(45) Date of Patent: Nov. 4, 2014

(54) QUANTIFICATION OF BOTULINUM TOXIN

(75) Inventors: Andrew Martin Pickett, Berkshire (GB); Robin Andrew Quirk, Nottingham (GB); Richard Melville France, Nottingham (GB); Lisa Anne Riccalton-Banks, Nottingham (GB)

(73) Assignee: Ipsen Biopharm Limited (GB)

( * ) Notice: Subject to any disclaimer, the term of this patent is extended or adjusted under 35 U.S.C. 154(b) by 658 days.

(21) Appl. No.: 10/545,009

(22) PCT Filed: Feb. 20, 2004

(86) PCT No.: PCT/GB2004/000697
§ 371 (c)(1),
(2), (4) Date: Dec. 20, 2005

(87) PCT Pub. No.: WO2004/074838
PCT Pub. Date: Sep. 2, 2004

(65) Prior Publication Data
US 2006/0263352 A1    Nov. 23, 2006

(30) Foreign Application Priority Data
Feb. 21, 2003    (GB) .................................. 0303997.1

(51) Int. Cl.
*C12Q 1/02*        (2006.01)
*A61K 39/02*       (2006.01)
*A61K 39/08*       (2006.01)
*G01N 33/94*       (2006.01)
*G01N 33/50*       (2006.01)

(52) U.S. Cl.
CPC .......... *G01N 33/944* (2013.01); *G01N 33/5088* (2013.01)
USPC ........................ 435/29; 424/236.1; 424/239.1

(58) Field of Classification Search
USPC ......................................................... 435/29
See application file for complete search history.

(56) References Cited

U.S. PATENT DOCUMENTS

| 5,251,621 A | 10/1993 | Collins |
| 5,814,086 A | 9/1998 | Hirschberg et al. |

FOREIGN PATENT DOCUMENTS

| WO | WO 95/12417 | 5/1995 |
| WO | WO 96/20754 | 7/1996 |
| WO | WO 99/03483 | * 1/1999 |

OTHER PUBLICATIONS

Dreyer et al. 1983, Pflugers Arch vol. 399, pp. 228-234.*
Goschel et al. 1997, Experimental Neurology vol. 147, pp. 96-102.*
Wohlfarth et al 1997 Naunyn-Schmiedeberg's Arch Pharmacol vol. 355 pp. 335-340.*
Hesse et al 1995 Neuroscience Letters vol. 201 pp. 37-40.*
Nick et al. 2000, Nature Neuroscience vol. 3, No. 2 pp. 142-148.*
Patrick Reilly 1992 Electrical Stimulation and Electropathy.*
Habermann et al 1980 Naunyn-Schmiedeberg's Arch Pharmacol vol. 311 pp. 33-40.*
Dimitrova et al (2002 Experimental Brain Research vol. 147 pp. 449-455).*
Simpson et al (1977 The Journal of Pharmacology and Experimental Therapeutics vol. 200 No. 2 pp. 343-351).*
Kimura et al (Biochemical and Biophysical Research Communications 1998 vol. 244 pp. 275-279).*
Yoshiaki et al (1988 Proc. Natl. Acad. Sci. USA vol. 85 pp. 1978-1982).*
Nordback et al (Gut 1998 vol. 42 pp. 507-510).*
Burgen et al., J. Physiol. 109: 10-24 (1949).
Chang et al., Naunyn-Schmiedeberg's Arch. Pharmacol. 282: 129-142 (1974).
Göschel et al., Experimental Neurology 147: 96-102 (1997).
Pearce et al., Toxicon 35(9): 1373-1412 (1997).
Sheridan et al., Journal of Applied Toxicology 19: S29-S33 (1999).
Wohlfarth et al., Naunyn-Schmiedeberg's Arch. Pharmacol. 355: 355-340 (1997).
MacKenzie et al., Neuroscience 7(4): 997-1006 (1982).
Santamaria et al., Advances in Anatomy, Embryology, and Cell Biology, The Prostate of the Rat, vol. 194, pp. 38-42 (2007).
Hakami et al., European Journal of Cardio-thoracic Surgery 16: 228-232 (1999).
Miller et al., Muscle Nerve 22: 1036-1046 (1999).
Suter et al., J Appl Physiol 90: 1036-1040 (2001).

* cited by examiner

*Primary Examiner* — Rodney P Swartz
(74) *Attorney, Agent, or Firm* — Perkins Coie LLP

(57) ABSTRACT

The invention relates to a method for determining the quantity of pre-synaptic neuromuscular blocking substance (notably botulinum toxin) contained in a sample. In one aspects, the method comprises the following steps: (i) determining the minimum voltage $V_m$ needed to induce the contraction of muscle tissue, said muscle tissue being connected to an electrical stimulator through a motor nerve and preferably immersed in an oxygenated physiological buffer containing glucose; (ii) adding the sample containing the pre-synaptic neuromuscular blocking substance; (iii) electrically stimulating, at a voltage at least equal to $V_m$, the muscle tissue at certain time intervals; (iv) comparing the effect induced by the sample to the effect induced by a reference substance and thereby determining the quantity of the pre-synaptic neuromuscular blocking substance in the sample.

7 Claims, 4 Drawing Sheets

QUANTIFICATION OF BOTULINUM TOXIN

This application is a national stage of PCT/GB2004/000697 filed Feb. 20, 2004. The entire contents of the above-identified application are hereby incorporated by reference.

The invention relates to a method for determining the quantity of pre-synaptic neuromuscular blocking substance contained in a sample.

The determination of the quantity of pre-synaptic neuromuscular blocking substance contained in a sample is generally made through the measurement of the lethal dose $LD_{50}$ for this substance in mice or rats. This method is in particular used presently for the determination of the quantity of active botulinum toxin. Such $LD_{50}$ methods are synonym of a large number of animals killed.

The present invention offers a new method which spares the life of a significant number of animals compared to the usual $LD_{50}$ methods.

Accordingly, there is provided according to the present invention a method for determining the quantity of a pre-synaptic neuromuscular blocking substance in a sample which comprises the following steps:
(i) determining the minimum voltage $V_m$ needed to induce the contraction of muscle tissue, said muscle tissue being connected to an electrical stimulator through a motor nerve;
(ii) adding the sample containing the pre-synaptic neuromuscular blocking substance;
(iii) electrically stimulating, at a voltage at least equal to $V_m$, the muscle tissue at certain time intervals;
(iv) comparing the effect induced by the sample to the effect induced by a reference substance and thereby determining the quantity of the pre-synaptic neuromuscular blocking substance in the sample.

By pre-synaptic neuromuscular blocking substance should be understood in the present application a substance that prevents and/or inhibits transmission of the chemical messages and signals involved in pre-synaptic neuromuscular activity. Examples of pre-synaptic neuromuscular blocking substances are substances that inhibit acetylcholine (ACH) synthesis or release; those include notably biological toxins (such as botulinum neurotoxins and bungarotoxins) and chemicals (such as hemicholinium or triethylcholine which inhibit ACH synthesis, aminoglycoside antibiotics which inhibit ACH release or tubocurarine and similar compounds). Preferred pre-synaptic neuromuscular blocking substances according to this invention will be botulinum neurotoxins and bungarotoxins (α-bungarotoxin being preferred among the bungarotoxins).

By botulinum neurotoxins (or botulinum toxins) is meant in the present application botulinum neurotoxin complexes (whether of type A, B, C, D, E, F or G) as well as high purity botulinum neurotoxins (whether of type A, B, C, D, E, F or G). Botulinum toxin type A includes all types of botulinum toxin type A, including A1, A2 and A3.

By botulinum neurotoxin complex (whether of type A, B, C, D, E, F or G) should be understood in the present application a botulinum neurotoxin (whether of type A, B, C, D, E, F or G) associated with at least another non-toxic protein.

By high purity botulinum neurotoxin (whether of type A, B, C, D, E, F or G) is meant, in the present application, botulinum neurotoxin (whether of type A, B, C, D, E, F or G) outside from complexes including at least another protein. In other words, a high purity botulinum neurotoxin (type A, B, C, D, E, F or G) does not contain significant quantities of any other *Clostridium* spp derived protein than botulinum neurotoxin (type A, B, C, D, E, F or G).

By muscle tissue is meant, in the present application, a muscular fibre sample comprising one or more muscle fibres.

Preferably, the muscle tissue is immersed in a buffer, such as a physiological buffer. The buffer may comprise an energy source. The energy source may be an ATP energy source, for example one or more of the following: ATP, a sugar such as glucose and/or creatine (including creatine phosphate), a fatty acid, an amino acid, glycogen and pyruvic acid. The buffer may be oxygenated, particularly for longer assays.

In a preferred embodiment, the buffer is an oxygenated physiological buffer containing glucose.

The buffer in which the muscle tissue is immersed will preferably contain at least 10 mM of glucose (e.g. 11 mM). Preferably also, the buffer will be saturated in oxygen (e.g. by bubbling oxygen or a 95/5 $O_2/CO_2$ mixture through the buffer). Furthermore, the buffer will preferably contain from 100 to 200 mM of NaCl, from 1 to 5 mM of KCl from 10 to 15 mM $NaHCO_3$, from 0.5 to 2 mM of $MgCl_2$ and from 1 to 5 mM of $CaCl_2$. The pH of the buffer will preferably be about 7.4.

Preferably, the method will be such that the electrical stimulation of step (iii) is carried out at a voltage at least equal to the supramaximal voltage $V_{SM}$. By supramaximal voltage is understood the minimum voltage to get the maximum twitch response of the muscle tissue.

According to a first variant of the invention (hereafter variant A), the effect induced used for the comparison of stage (iv) of the method is the time to paralysis of the muscle tissue (also named "lifetime" in this application). According to sub-variants, the time to paralysis may be determined based (variant A1) on the muscle contraction distance (paralysis being achieved once the contraction distance is equal to zero) or (variant A2) on the muscle twitch frequency (paralysis being achieved once the twitch frequency is equal to zero).

According to another variant of the invention (hereafter variant B), the effect induced used for the comparison of stage (iv) of the method is the variation in the contraction rate of the muscle tissue.

According to another variant of the invention (hereafter variant C), the effect induced used for the comparison of stage (iv) of the method is the variation in the contraction distance of the muscle tissue.

According to still another variant of the invention (hereafter variant D), the effect induced used for the comparison of stage (iv) of the method is the variation in the force of contraction of the muscle tissue.

According to a further variant of the invention (hereafter variant E), the effect induced used for the comparison of stage (iv) of the method is the variation in the end plate potential or the miniature end plate potential of the muscle tissue.

Combinations of the variants A (including its subvariants), B, C, D and E may be used by the person skilled in the art in order to achieve an improvement in the accuracy of the results obtained. In particular, the person skilled in the art may think of combining subvariant A1 and subvariant A2.

Preferably, the pre-synaptic neuromuscular blocking substance will be a botulinum neurotoxin. In particular, the botulinum neurotoxin may be selected from botulinum neurotoxin type A, botulinum neurotoxin type B and botulinum neurotoxin type F. More preferably, the botulinum neurotoxin will be selected from botulinum neurotoxin type A and botulinum neurotoxin type B. In a particularly preferred manner, the botulinum neurotoxin will be botulinum neurotoxin type A, notably a botulinum neurotoxin type A complex (like the active principles of the commercial products DYSPORT® (active principle: botulinum toxin type A) or BOTOX® ((Botulinum Toxin Type A))).

In a general manner, the method will be more sensitive at lower concentrations (for example 0 to 100 $LD_{50}$ units/ml, and preferably 0 to 50 or 0 to 10 $LD_{50}$ units/ml) while it may not work when high concentrations in pre-synaptic neuromuscular blocking substances are present in the sample (the muscle tissue remaining paralysed despite electrical stimulation). As a consequence, the sample to be tested will preferably be prepared in at least two or three dilutions (for example, non diluted, diluted 10 times and diluted 100 times) on which the invention method will be carried out; in that way, higher concentrations in pre-synaptic neuromuscular blocking substances can also be determined. However, the sensitivity of the method described previously can be improved as mentioned below.

According to a preferred execution mode of the invention, the muscle tissue will be constituted by a piece of rib muscle obtained from a mouse or a rat. Preferably, this piece will have a dimension of at least 2 mm by 10 mm. The muscle tissue could for example have a size corresponding to a 2-rib section of the rib muscle.

According to a further preferred execution mode of the invention, each electrical stimulation will always consist in applying a voltage $V_S$ which is at least equal to the minimum voltage $V_m$ that is needed to induce the contraction of the muscle tissue, $V_S$ being besides inferior or equal to a voltage which is slightly above $V_m$. The "voltage that is slightly above $V_m$" may be $V_m$ plus 3 Volts, $V_m$ plus 2 Volts or $V_m$ plus 1.5 Volt. For example, the stimulation voltage applied may be chosen as $V_m$ plus 1 Volt.

Further possible features of the invention include the use of a video camera combined with a video recorder. The films produced can then be analysed and the effect of the pre-synaptic neuromuscular blocking substance precisely evaluated. The quantity of pre-synaptic neuromuscular blocking substance present in the sample can then be derived from the effect observed for the sample compared to that observed for the reference.

Alternatively, for the variant D stated above, the force displacement transducer used to measure the force of contraction of the muscle tissue can be associated with an automatic real-time electronic data capture system.

In order to reduce result variability, the electrical stimulator will send at specified time intervals the chosen voltage $V_S$, which each time will bring about a certain effect. Using the mean effect observed in these conditions will allow to make a more accurate determination of the quantity of pre-synaptic neuromuscular blocking substance present in the sample.

A way of increasing sensitivity for the method consists in carrying out the method over a longer period of time, allowing more data to be captured (for example over a period of at least 5, 10 or 30 minutes and of up to 1, 2, 4, 8, 12, 24, 48, 72 hours or even more). For example, for variant D of the method, the method could be carried out until a reduction in a certain proportion of the force of contraction of the muscle tissue is measured (e.g. a reduction of 10, 20, 25, 30, 40, 50, 60, 70, 75, 80 or 90%).

In order to carry out this preferred execution mode, the life span of the muscle tissue needs to be extended compared to the more general method explained earlier.

In one particular approach aimed at extending said life span, oxygen and glucose (or other ATP source) are provided in a regular manner to the muscle tissue.

One way to achieve this is to exchange at regular intervals an oxygenated physiological buffer bath containing glucose (or other ATP source) with a new one in order to have the consumed oxygen and glucose (or other ATP source) replaced (wherein said intervals are preferably not less than 1 minute and not more than 24 hours, e.g. every 1, 2, 5, 10, 15 or 60 minutes). Another way consists in using a bath wherein oxygen is constantly bubbled, which allows to keep the oxygen concentration of the bath constant; additionally, glucose (or other ATP source) may be added at regular intervals to replace the glucose (or other ATP source) consumed by the muscle tissue.

Alternatively, a flow-through bath system can be used, which has the advantage of keeping constant glucose (or other ATP source) and optionally oxygen levels. In this system, the oxygenated physiological buffer containing glucose (or other ATP source) is pumped in at one end of the vessel in which the muscle tissue is immersed and pumped out at the other end.

Other means to extend the life span of the muscle tissue include the use of a train pulse stimulation which reduces the sample's fatigue. By train pulse stimulation is meant stimulations lasting a time $t_S$ separated from each other by periods lasting a time $t_P$ during which no stimulation is exerted. The time $t_S$ will preferably be from 50 μs to 500 ms, more preferably from 100 μs to 250 ms and even more preferably from 100 μs to 1 ms (e.g. 200 μs or about 200 μs); the time $t_P$ will preferably be from 0.1 to 10 s, and more preferably from 0.5 and 2 s (e.g. 1 s or about 1 s); the ratio $t_S/t_P$ will preferably be from 1:2 to 1:50 000, more preferably from 1:5 to 1:20 000 and even more preferably from 1:500 to 1:10 000 (e.g. about 1:5 000).

The present invention also provides a method for determining the quantity of neutralising antibodies to a pre-synaptic neuromuscular blocking substance in a sample which comprises the following steps:

(i) determining the minimum voltage $V_m$ needed to induce the contraction of muscle tissue, said muscle tissue being connected to an electrical stimulator through a motor nerve;

(ii) adding a mixture of the sample to be tested containing the neutralising antibodies to the pre-synaptic neuromuscular blocking substance and a determined quantity of said pre-synaptic neuromuscular blocking substance, said mixture having been pre-incubated at a temperature from 0 to 45° C. for a period from about 15 to about 120 minutes;

(iii) electrically stimulating, at a voltage at least equal to $V_m$, the muscle tissue at certain time intervals;

(iv) comparing the effect induced by the mixture to the effect induced by the determined quantity of said pre-synaptic neuromuscular blocking substance and thereby determining the quantity of neutralising antibodies to the pre-synaptic neuromuscular blocking substance in the sample.

All the variants indicated previously for the method for determining the quantity of a pre-synaptic neuromuscular blocking substance in a sample are applicable *mutatis mutandis* to the invention method for determining the quantity of neutralising antibodies to a pre-synaptic neuromuscular blocking substance in a sample.

The term "about" refers to an interval around the considered value. As used in this patent application, "about X" means an interval from X minus 10% of X to X plus 10% of X, and preferably an interval from X minus 5% of X to X plus 5% of X.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

The following examples are presented to illustrate the above and must in no case be considered as a limit to the scope of the invention.

EXAMPLES

Figure 1:
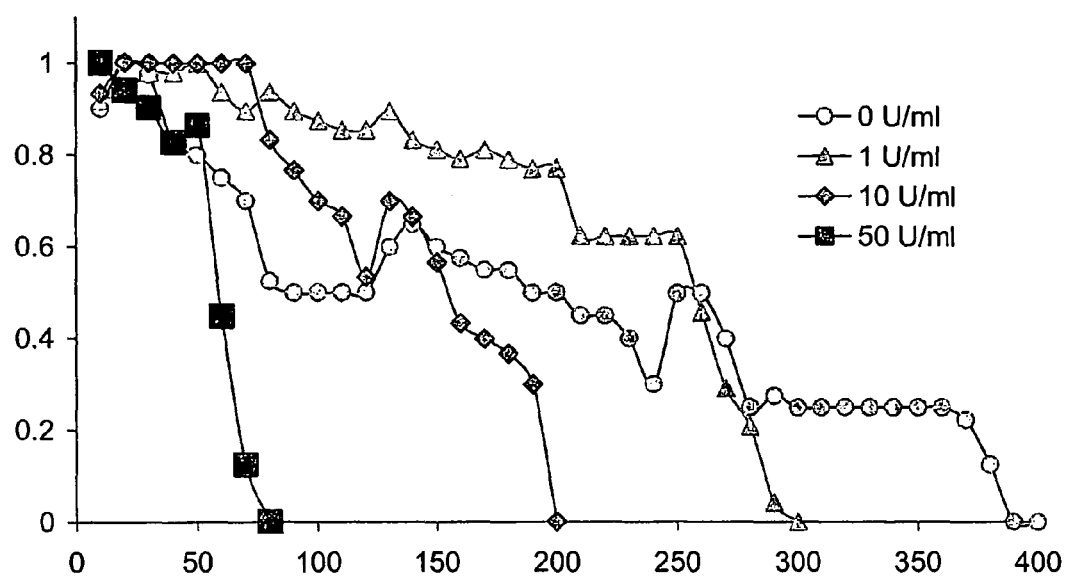
FIG. 1 shows the relative contraction distance of an intercostal rat preparation measured in function of time with varying DYSPORT® (active principle: botulinum toxin type A) concentrations (0, 1, 10 and 50 U) according to the procedure described in Example 1. The X-axis shows Time (s), while the Y-axis shows Distance (normalised to contraction initial size).

In the following Examples, 1 Speywood unit or 1 U corresponds to the median intraperitoneal $LD_{50}$ dose of botulinum toxin in mice.

Example 1

Botulinum Toxin Containing Sample

Materials Used
a) Buffer Solutions Used:
The modified Ringers buffer identified hereafter as "Lillies Ringers buffer" is prepared by diluting the following in water:

| | |
|---|---|
| NaCl | 138.8 mM |
| KCl | 4 mM |
| $NaHCO_3$ | 12 mM |
| $KH_2PO_4$ | 1 mM |
| $MgCl_2$ | 1 mM |
| $CaCl_2$ | 2 mM |

Immediately prior to use, glucose (11 mM) is added to the solution prepared previously and a gas mixture of 95% $O_2$ and 5% $CO_2$ is bubbled through the buffer solution to yield the Lillies Ringers buffer.

The Phosphate Buffered Saline solution (PBS) referred to hereafter is prepared by dissolution of a tablet supplied by Sigma which, when added to 200 ml of water, provides the following characteristics to the buffer:

| | |
|---|---|
| Phosphate buffer | 0.01 M |
| KCl | 0.0027 M |
| NaCl | 0.137 M |
| pH at 25° C. | 7.4 | b) Isolation of Tissue:
Wistar rats (approximate weight 275 g) are sacrificed by neck dislocation following $CO_2$ exposure (approximately 3 min to induce loss of consciousness). The rib cage is dissected from each animal, placed in Lillies Ringers buffer and transported to the experiment place (journey time: approximately 15 min). There the rib cage is separated into two sections by careful dissection along the spinal column. The tissues are stored in oxygenated buffer prior to carrying out the experimental procedures.

c) Determination of Minimum Voltage $V_m$ Needed to Induce Muscle Contraction:

Each intercostal preparation (half rib cage) is placed into a Petri dish containing Lillies Ringers buffer. For each preparation, one intercostal nerve is carefully dissected to reveal approximately 1-2 mm of nerve bundle. Following dissection, the preparation can be revived in freshly oxygenated Lillies Ringers buffer for approximately 15-20 minutes before being returned to a Petri dish containing 10 ml of oxygenated Lillies Ringers buffer. The dissected intercostal nerve is then connected via a suction electrode to a stimulator (Grass Instruments Model S48), with a return contact electrode placed in the media. The minimum voltage $V_m$ needed to induce muscle contraction is determined. If stimulation cannot be achieved below 10V, another nerve is dissected and the preparation revived prior to continuation.

Method for Determining the Quantity of Botulinum Toxin Contained in a Sample

The nerve is stimulated with a pulsed voltage (5-9V, 1 Hz), the voltage chosen always being 1 V above the threshold voltage $V_m$ required to achieve stimulation and muscle contraction. Video microscopy of the section is carried out with a Nikon SMZ800 stereomicroscope equipped with JVC TKC1481EG video camera connected to a combined TV/video recorder.

DYSPORT® (active principle: botulinum toxin type A) is added in PBS directly above the intercostal preparation (slightly submerged within 10 ml of buffer). For the 50 Speywood units (U) per ml dose, 500 U of toxin is added to the culture dish (10 ml buffer) to yield a final concentration of 50 U/ml. For the 10 U/ml dose, 100 U is added to the culture dish to yield a final concentration of 10 U/ml. For the 1 U/ml dose, 10 U is added to the culture dish yielding a final concentration of 1 U/ml. For the placebo (which has the same composition as DYSPORT® (active principle: botulinum toxin type A), except that botulinum toxin is absent), the full contents of the vial (in 0.2 ml PBS) is added to the culture dish.

Data Analysis

The recorded video clips are converted to MPEG files. To assist with subsequent analysis, each movie is cut into 2-minute sections and these sections are slowed to ½ their initial speed using ADOBE® PREMIERE® 5.1 software.

Analysis is then performed by counting the number of twitches in a 10 s period (20 s on half speed clips) and averaging the number of twitches over this 10 s period to yield a value of twitch frequency. Contraction distance can also be measured by playing the movie with a superimposed scale bar (of arbitrary units—nominally a 6-7 point scale), the data being averaged to give the contraction distance over each 10 s period, or alternatively said distance is compared to the initial contraction distance.

The experiments are repeated a certain number of times (0 U/ml: n=5; 1 U/ml: n=5; 10 U/ml: n=4; 50 U/ml: n=4) and the results are averaged.

Results

From FIG. 1 one will see that the relative contraction distance (i.e. the contraction distance in the presence of toxin divided by the contraction distance in the absence of toxin) is reduced more or less quickly as a function of the DYSPORT® (active principle: botulinum toxin type A) concentration.

Figure 2:
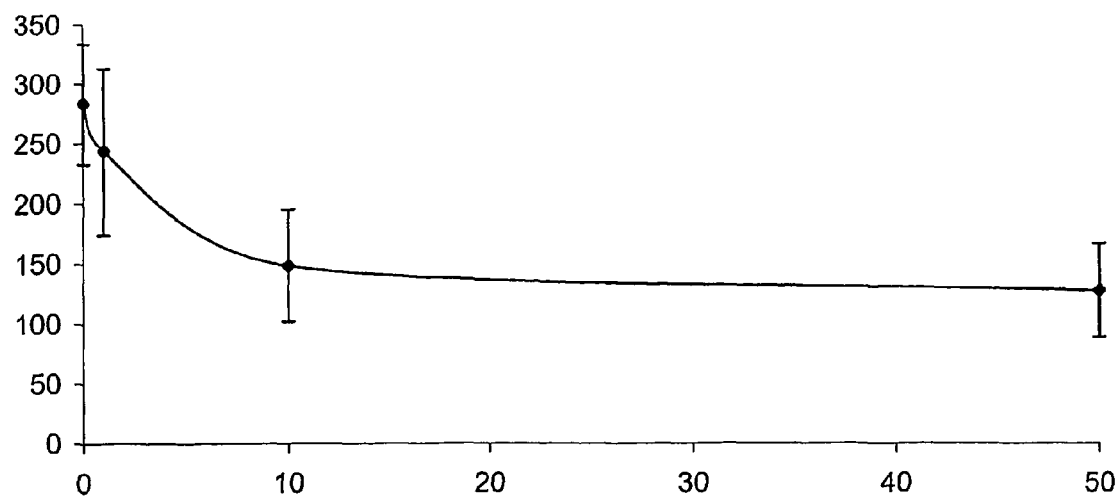
FIG. 2 shows the lifetime of an intercostal rat preparation measured from contraction distance with varying DYSPORT® (active principle: botulinum toxin type A) concentrations (0, 1, 10 and 50 U) according to the procedure described in Example 1. The data shown are means±sem, n=4-5). The X-axis shows DYSPORT® (active principle: botulinum toxin type A) Concentration Time (LD50 Units/ ml), while the Y-axis shows Time (s).

As can also be seen from FIG. 2 which shows results regarding the distance twitch lifetime (i.e. the time needed from the moment the toxin is added until the point when the contraction distance becomes zero), a dose-dependant reduction in the muscle contraction distance as a function of the DYSPORT® (active principle: botulinum toxin type A) concentration can be observed.

Figure 3:
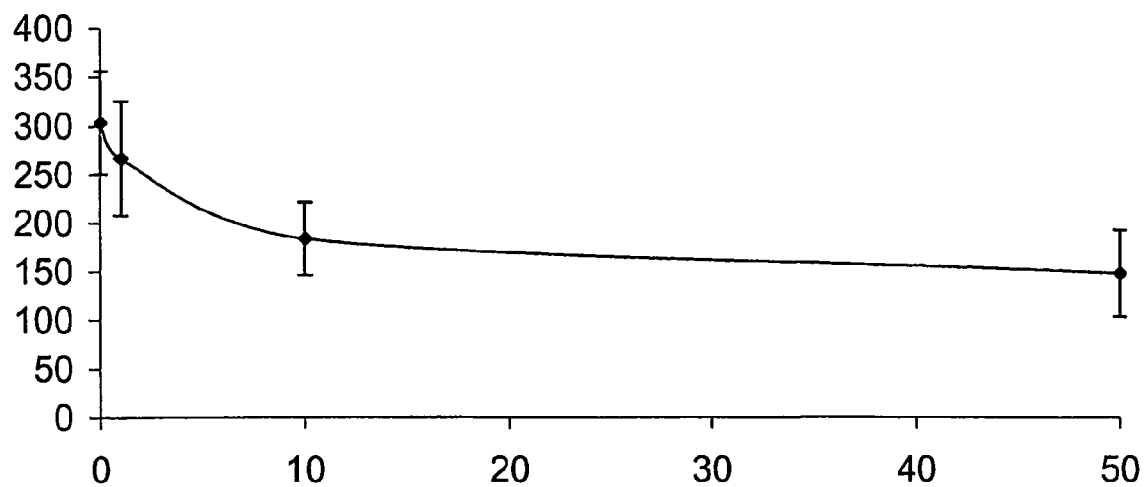
FIG. 3 represents the lifetime of an intercostal rat preparation measured from twitch frequency with varying DYSPORT® (active principle: botulinum toxin type A) concentrations (0, 1, 10 and 50 U) according to the procedure described in Example 1. The data shown are means±sem, n=4-5). The X-axis shows DYSPORT® (active principle: botulinum toxin type A) Concentration Time (LD50 Units/ ml), while the Y-axis shows Time (s).

The twitch frequency lifetime (i.e. the time needed from the moment the toxin is added until the point when the twitch frequency becomes zero) is also reduced by DYSPORT® (active principle: botulinum toxin type A) in a dose-dependant manner as is shown in FIG. 3.

Example 2

α-Bungarotoxin Containing Sample

Using the same procedure as described for Example 1, α-bungarotoxin instead of DYSPORT® (active principle: botulinum toxin type A) is tested at the concentration of 21 µM (n=3). The mean twitch lifetime of the α-bungarotoxin preparation is 225 s (±sem 93, n=3) and 238 s (±sem 93, n=3), measured from contraction distance and twitch frequency respectively.

Example 3

Extended Life System

Material Preparation
a) Buffer Solutions Used:
The modified Ringers buffer or "Lillies Ringers buffer" used in this Example is the same as for Example 1.
The Gelatine Phosphate Buffer (GPB) used in this Example is prepared by diluting the following in 1 liter of water:

| | |
|---|---|
| Gelatin | 2 g |
| NaHPO$_4$, 2H$_2$O | 10 g |

Figure 4:
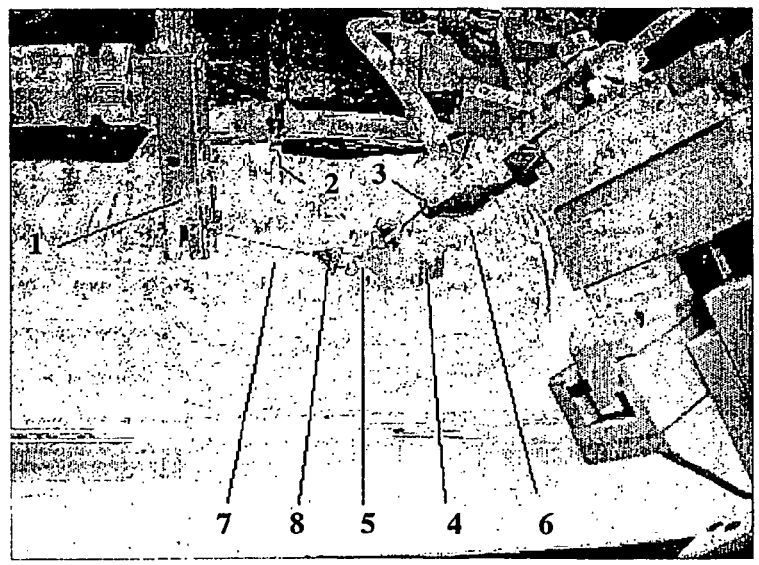
FIG. 4 shows a 2-rib tissue section attached to the force displacement transducer in a static bath setup.

B) Isolation of the Tissue:
Male Wistar rats (approximately 230-300 g) are sacrificed by neck dislocation following CO$_2$ exposure (approximately 3 minutes to induce loss of consciousness). The rib cage is dissected from the animal, placed in Lillies Ringers buffer and transported to the experiment place (journey time: approximately 20 minutes). There the rib cage is separated into two sections by careful dissection along the spinal column and sternum. The two halves of the rib cage are stored in approximately 300 ml of continually oxygenated Lillies Ringers buffer for at least 30 minutes prior to experimental procedures.

c) Determination of Minimum Voltage $V_m$ Needed to Induce Muscle Contractions:
One half of the rib cage is placed in a Petri dish containing approximately 10 ml of Lillies Ringers buffer and an intercostal nerve is carefully dissected to reveal approximately 1-2 mm of nerve bundle. This nerve is then connected via a suction electrode to a stimulator (Grass Instruments Model S48) with a return electrode placed in the media. The minimum voltage $V_m$ needed to induce muscle contraction is determined. If stimulation cannot be achieved below 10 V (1 Hz, 200 µsec duration), another nerve is dissected. The 2-rib section containing the dissected nerve is dissected from the half rib cage, ensuring as much excess muscle tissue as possible remains either side of the 2 ribs for later attachment to the force displacement transducer.

d) Attachment to the Force Displacement Transducer:
With reference to the static bath system shown in FIG. 4, three metal staples were attached to the non-stimulated muscle tissue on either side of the two ribs. One side of the 2-rib section (5) was attached to the fixed foot (4) via the three staples whilst the other side was affixed to the free foot (8). The fixed foot was clamped securely in place while the free foot was attached to the force displacement transducer (1; Grass Instruments Model FT03) via approximately 4 cm of cotton thread (7). The fixed tissue was immersed in approximately 500 ml Lillies Ringers buffer, and a return electrode (2) placed within the buffer. The dissected intercostal nerve was connected via a (positive) suction electrode (3) to the stimulator. The system shown in FIG. 4 also includes a CO2/O2 gas inlet (6).

Method for Determining the Quantity of Botulinum Toxin Contained in a Sample

The 2-rib tissue sections are stimulated for approximately 90 minutes at 15 V, 200 µsec duration using train pulse stimulation (1 pulse/second for the first 5 seconds of every 30 second period).

The required concentration of toxin is reconstituted in GPB immediately prior to application. The toxin delivery is via one of two methods:
A) Direct application—The 2-rib section is exposed to the air/liquid interface by removal of some of the buffer within the tissue bath. Using a Hamilton syringe, the toxin is applied directly onto the exposed tissue in a drop wise fashion, coating the muscle in the toxin solution. The tissue is left exposed for a further 15 minutes to enable uptake of the toxin before covering that with the original Ringers buffer. If necessary, any dislodged, dissected nerves are reconnected to the suction electrode.
B) Immersion—Using a Hamilton syringe, the toxin is applied directly into the tissue bath in close proximity to (but not directly onto) the 2-rib section.

Twitch force readings recorded from the force displacement transducer are first amplified throughout a Grass Instruments AC/DC strain gage amplifier (Model P122) and signals are then recorded using Grass PolyVIEW™ software.

Data Analysis

From the traces recorded, the time taken for the initial maximal twitch force measurement (after addition of toxin/placebo) to decrease by a certain percentage was measured. The experiments are repeated a certain number of times (direct application method: placebo: n==4; 500 U: n=8; 1000 U: n=5; 1500 U: n=11; immersion method: placebo: n=3; 3 U/ml: n=5; 6 U/ml: n=2, 12 U/mil: n=2). Due to the long life span of the tissue when exposed to placebo and low levels of toxin, values illustrated at the 90% reduction in twitch force are estimated results based on the extrapolation of the data assuming a constant rate of decline.

Results

A) Direct Application Method

Figure 5:
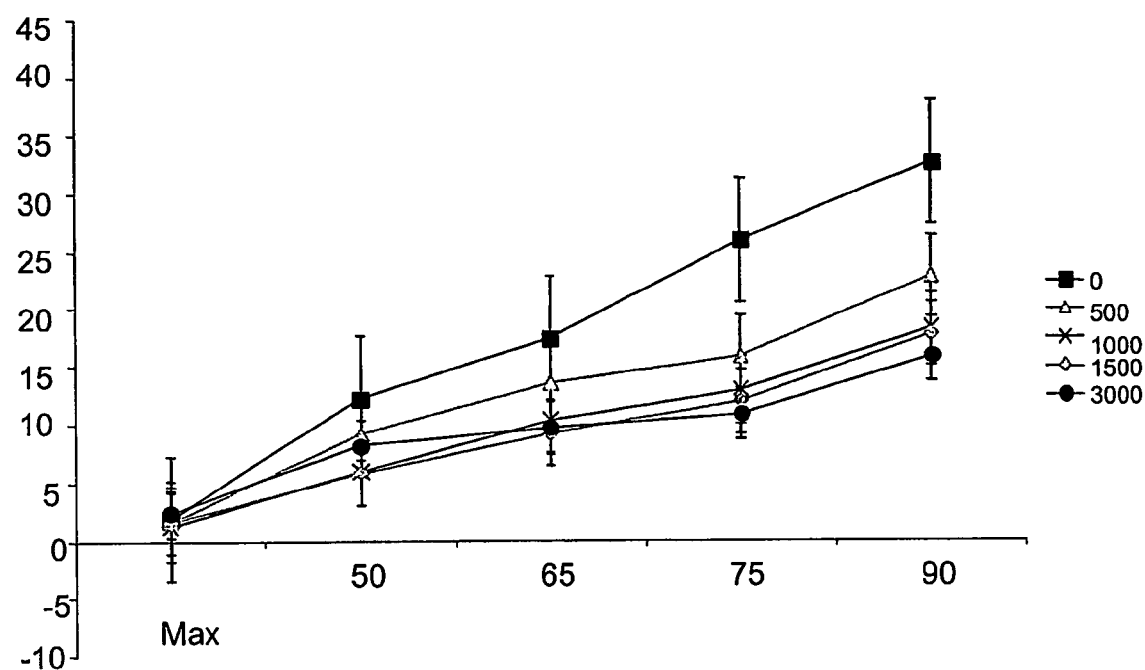
FIG. 5 shows the time taken (hours) for the maximal twitch force measurements of 2-rib sections exposed to either placebo or 500, 1000, 1500 or 3000 U of toxin using the direct application method of Example 3 in the static system (the following numbers of experiments n apply: placebo: n=4; 500 U: n=8; 1000 U: n=5; 1500 U: n=11). Error bars illustrate ±S.E.M. The X-axis shows % Reduction in Maximal Twitch Force, while the Y-axis shows Time (Hours).

Over time, a gradual reduction in twitch force measurements are recorded in all samples, including after the addition of placebo as seen in FIG. 5. Following placebo exposure, a 50% reduction in maximal twitch force is observed after over approximately 12 hours. In comparison, twitch force is reduced more rapidly in those tissue samples exposed to 1500 U of toxin, with a 50% reduction being reached after approximately 5 hours.

B) Immersion Method

Figure 6:
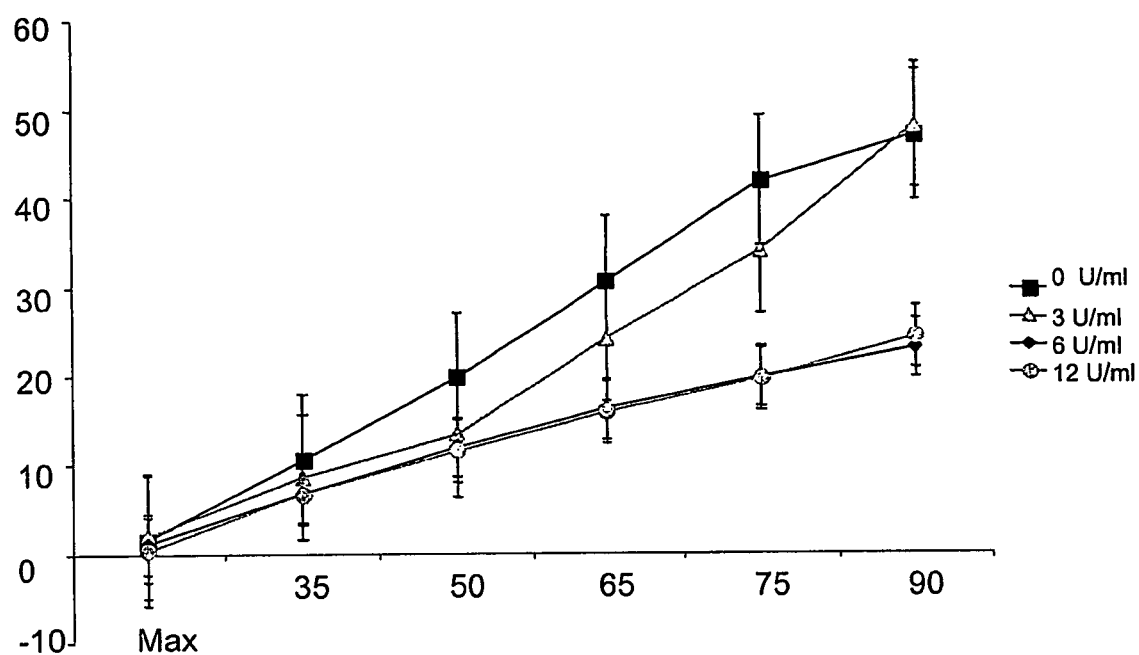
FIG. 6 shows the time taken (hours) for the maximal twitch force measurements of 2-rib sections exposed to either placebo or 3, 6 or 12 U/ml of toxin using the immersion method of Example 3 in the static system (the following numbers of experiments n apply: placebo: n=3; 3 U/ml: n=5; 6 U/ml: n=2; 12 U/ml: n=2). Error bars illustrate±S.E.M. The X-axis shows % Reduction in Maximal Twitch Force, while the Y-axis shows Time (Hours).

Reductions in twitch force measurements were recorded after the addition of placebo with a 50% reduction in maximal twitch force observed after approximately 20 hours as seen in FIG. 6. Immersing the tissue in a 3 unit/ml solution of toxin further increased the rate of twitch force reduction with a 50% reduction in twitch force reached after 13 hours of stimulation. At higher toxin concentrations, a dose dependent response is still evident.

As one can see, a repeatable dose dependent toxin-induced suppression of muscle contraction is observed using both the direct application and immersion methods of toxin delivery.

This application claims priority to GB0303997.1, filed Feb. 21, 2003, the entirety of which is hereby incorporated by reference.

The invention claimed is:

1. A method for determining the quantity of a botulinum neurotoxin expressed in $LD_{50}$ units/ml in a sample comprising a quantity of the botulinum neurotoxin, wherein the method comprises the following steps:
   (i) selecting a muscle tissue capable of being electrically stimulated to induce the contraction of the muscle tissue, and determining the minimum voltage $V_m$ needed to induce the contraction of muscle tissue, the muscle tissue being immersed in a buffer and connected to an electrical stimulator through a motor nerve;
   (ii) adding the sample containing a quantity of the botulinum neurotoxin having a concentration of 0 to 100 $LD_{50}$ units/ml;
   (iii) electrically stimulating, at a voltage at least equal to $V_m$, the muscle tissue at certain time intervals by train pulse electrical stimulations thereby extending the life span of the muscle tissue, allowing long testing, or reducing muscle fatigue, wherein each stimulation period is for a time $t_S$ and is separated from the next stimulation period by a period lasting a time $t_P$ during which no stimulation is exerted, wherein the ratio $t_S/t_P$ is from 1:2 to 1:50,000;
   (iv) measuring the effect induced by the sample and the effect induced by varying concentrations of a reference substance, wherein the effect is the variation in the force of contraction of the muscle tissue and wherein said reference substance is a botulinum neurotoxin type A; and
   (v) comparing the effect induced by the sample to the effect induced by said varying concentrations of the reference substance and thereby determining the quantity of the botulinum neurotoxin in the sample; wherein the method is carried out for at least 24 hours for data capture and until a reduction of 90% of the force of contraction of the muscle tissue is measured, thereby increasing the sensitivity of the method.

2. The method of claim 1, wherein the botulinum toxin is selected from botulinum toxin type A, botulinum toxin type B and botulinum toxin type F.

3. The method of claim 1, wherein the botulinum toxin is botulinum toxin type A.

4. The method according to claim 1, wherein the muscle tissue is a piece of rib muscle obtained from a mouse or a rat.

5. The method of claim 1, wherein concentration of the botulinum neurotoxin present in a sample is between 0 to 100 $LD_{50}$ units/ml.

6. The method of claim 1, wherein concentration of the botulinum neurotoxin present in a sample is between 0 to 50 $LD_{50}$ units/ml.

7. The method of claim 1, wherein concentration of the botulinum neurotoxin present in a sample is between 0 to 10 $LD_{50}$ units/ml.

* * * * *